United States Patent [19]

Schmitz

[11] 4,194,505
[45] Mar. 25, 1980

[54] CONTAINERIZED HYPODERMIC MODULE

[75] Inventor: William L. Schmitz, Hemet, Calif.

[73] Assignee: Vac-O-Cast, Inc., Hemt, Calif.

[21] Appl. No.: 942,533

[22] Filed: Sep. 15, 1978

[51] Int. Cl.² ............................................. A61M 5/20
[52] U.S. Cl. ......................... 128/218 D; 128/218 DA;
                                                      128/218 F
[58] Field of Search ........... 128/218 R, 218 F, 218 D,
                                128/218 DA, 218 A, 215, 216, 234

[56]  References Cited
U.S. PATENT DOCUMENTS

| | | | |
|---|---|---|---|
| 2,866,458 | 12/1958 | Hein, Jr. | 128/218 F |
| 3,094,989 | 6/1963 | Stauffer | 128/218F |
| 3,136,313 | 6/1964 | Enstrom et al. | 128/218 F |
| 3,729,003 | 4/1973 | Hurschman | 128/218 F X |

Primary Examiner—Yasko, John D.

[57] ABSTRACT

A self-contained predetermined dosage hypodermic ampule with enclosed sterile needle projected by a companion injector device from the sealed forward end of the ampule, with liquid medicament pressurizing means for dispensing the medicament from the needle and into the tissue of the patient during penetration of the tissue by the needle, all portions of the length of the needle being hygienically sealed from external contamination at all times; the companion injector means having simply operated and dependable safeguards against accidental operation, and the injector means and hypodermic needle cooperating to insure smooth, non-sticking operation of the medicament pressurizing means.

21 Claims, 14 Drawing Figures

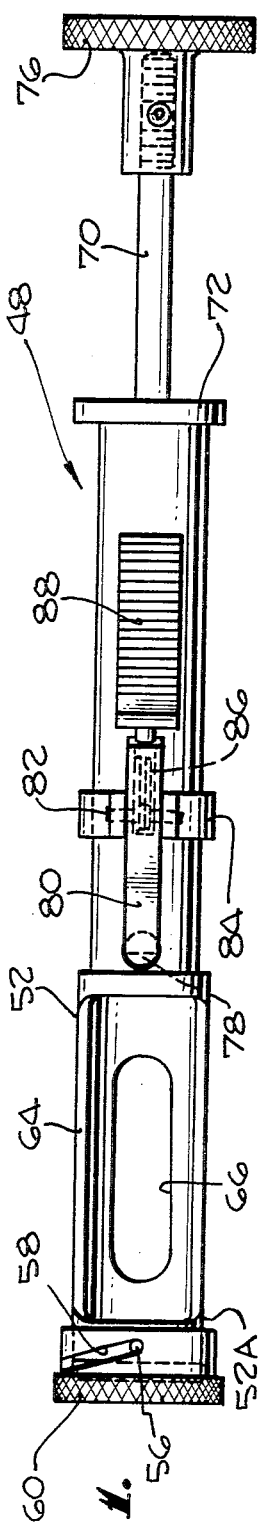
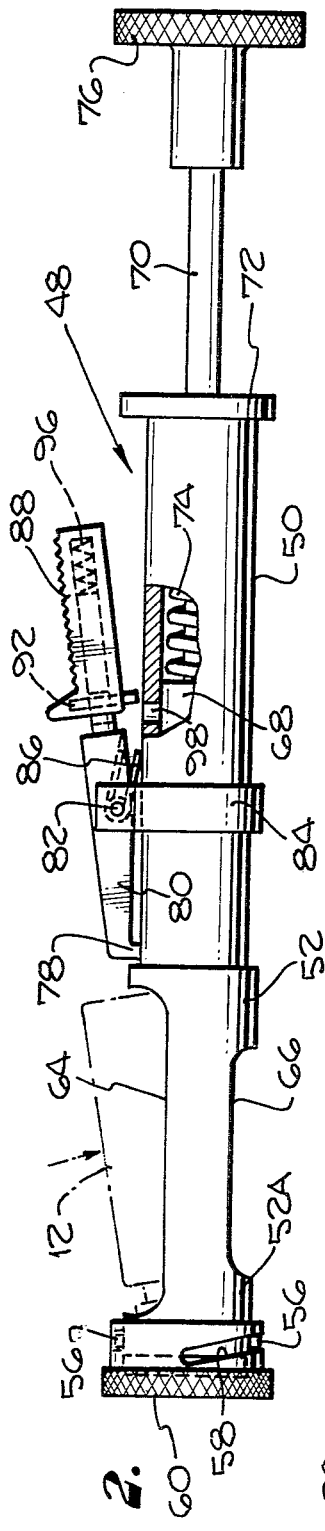
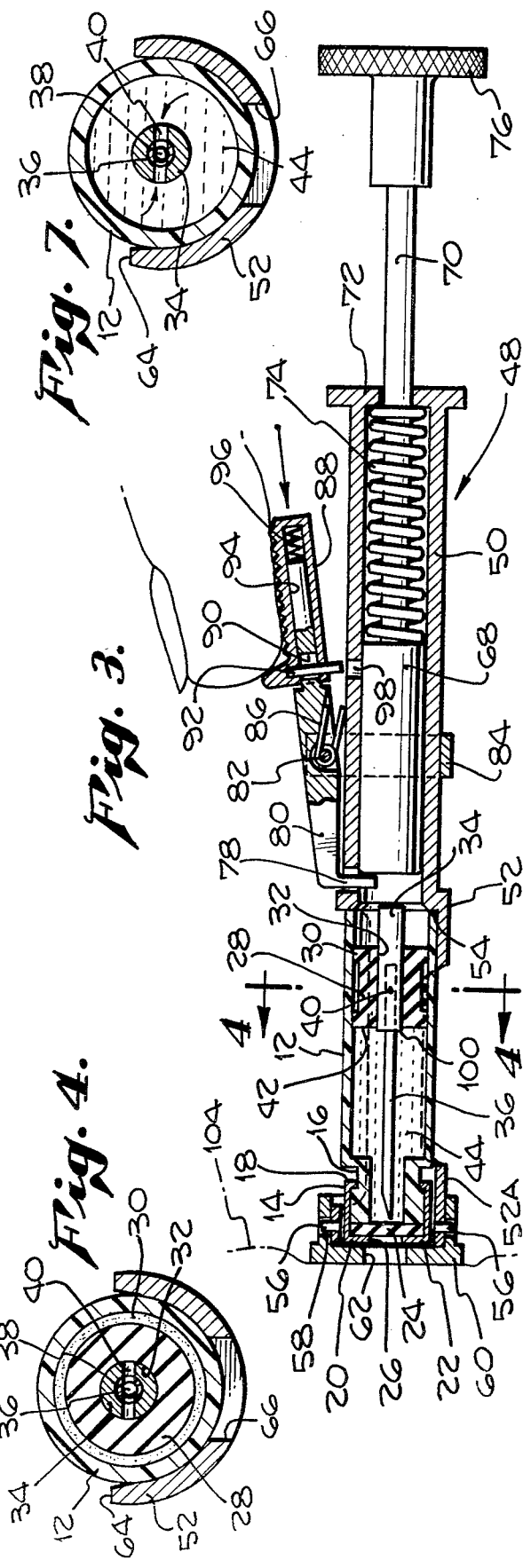

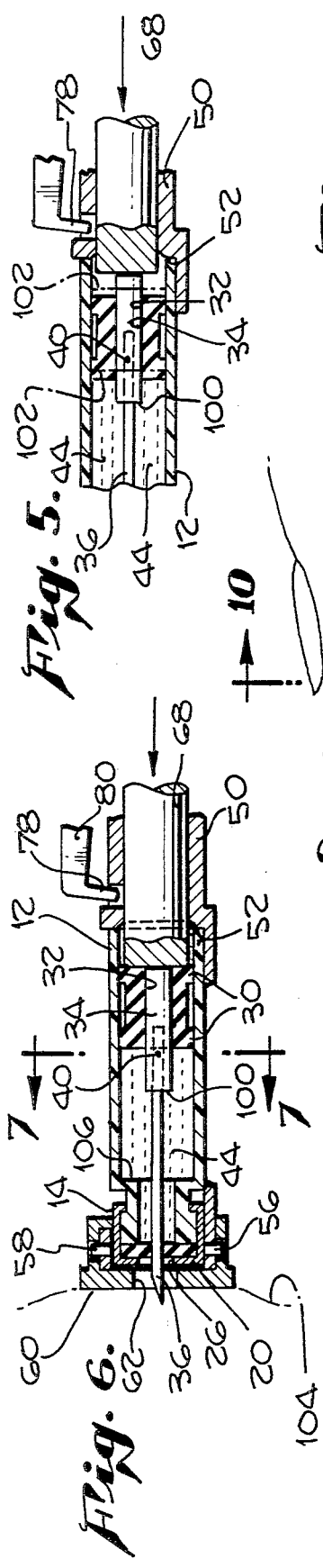

CONTAINERIZED HYPODERMIC MODULE

KNOWN PRIOR ART

Prior U.S. Pat. Nos. relating to the ampule feature per se are:

2696212 — Dunmire — Dec. 7, 1954
2769443 — Dunmire — Nov. 6, 1956

Prior art as to the related injector assembly is:

1845930 — Morrow — Feb. 16, 1932
2701566 — Krug — Feb. 8, 1955
2866458 — Hein, Jr. — Dec. 30, 1958
2888924 — Dunmire — June 2, 1959
3051173 — Johnson — Aug. 28, 1962
3605744 — Dwyer — Sept. 20, 1971
3729003 — Hurschman — Apr. 24, 1973

One of the important features of the ampule per se is the provision of predetermined medicament dosage with a self-contained needle sealed against contamination with provision for smoothly guided, straight line projection of the needle from the ampule and into the tissue of the patient, the main body portion of the ampule comprising a glass cylinder having means for supporting a sealing diaphragm at its forward end and having a smoothly sliding, medicament sealing piston which supports the needle and proper axial alignment for controlled axial movement of the needle relative to the piston.

The companion injector provides means for easy loading thereof with the ampule, secure positioning of the ampule and means for safeguarding the injector against accidental actuation.

While the system can, of course, be utilized by trained personnel, it is of particular value to patients who self-administer medicaments frequently, such as is the case with diabetics. It provides for uniformity of dispersion in the tissue as needle penetration proceeds, thereby greatly reducing patient discomfort. It provides for precise dosage because of pre-filling of the ampule. Self-containment of the needle in the ampule and chances of contamination and infection are reduced to a minimum. Additionally, the injector unit, loaded with a pre-dosed ampule and sterile needle, can be carried in the pocket or purse of the patient with safety because of the dual action safety mechanism thereof.

The above and other objects will more fully appear from the following description in connection with the accompanying drawings.

FIG. 1 is an unloaded elevational view of an embodiment of the injector unit.

FIG. 2 is a view of the device in FIG. 1 rotated 90 degrees, with a partially inserted ampule in broken lines and with interior injector structure shown in sectional detail and in broken lines.

FIG. 3 is a longitudinal sectional view through the complete assembly with the ampule in injection position and the injector safety element in injector trigger actuating position.

FIG. 4 is an enlarged sectional view approximately on the line 4—4 of FIG. 3.

FIG. 5 is a sectional detail of the injector plunger in its initial contact with the rearward end of the hypodermic needle, a reflex position of the ampule piston being indicated in broken lines.

FIG. 6 is a longitudinal sectional view through the ampule in the forward end of the injector showing the needle at the point of skin penetration.

FIG. 7 is an enlarged sectional view taken approximately on the line 7—7 of FIG. 6.

FIG. 8 is a longitudinal sectional view showing the position of full penetration of the needle and the completion of injection of the medicament.

FIG. 9 is an enlarged sectional view taken approximately on line 9—9 of FIG. 8.

FIG. 10 is an enlarged sectional view taken approximately on the line 10—10 of FIG. 8.

FIG. 11 is a side elevational view of a typical ampule.

Figure 12:
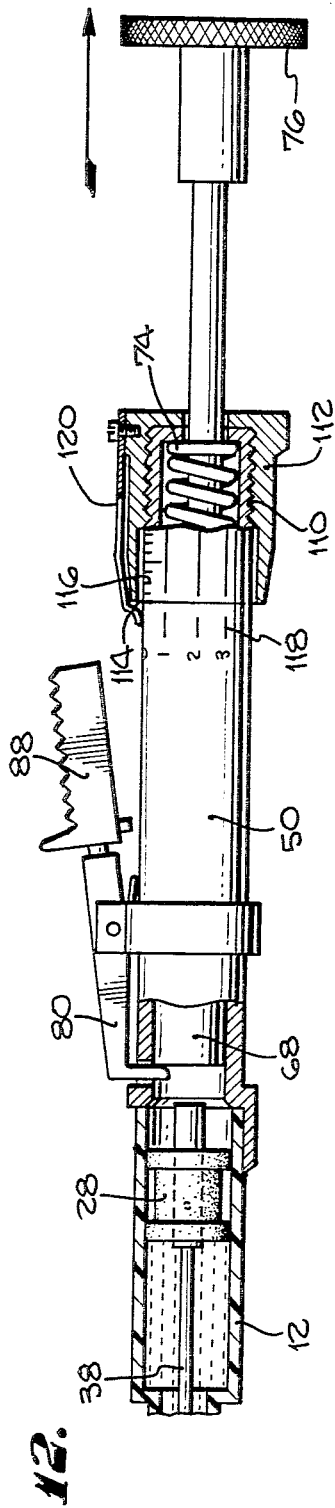
FIG. 12 is a side elevational view, with portions in section, of an embodiment incorporating an adjustable dosage control set for emptying the entire ampule.

There is illustrated an ampule 12, preferably of glass, and of cylindrical shape. The forward end portion of the ampule is reduced in diameter as at 14 and the exterior provided with a circumferential groove 16 to receive the crimped edge 18 of a forward end cap 20, the latter having a forward portion 22 which holds an elastomeric seal 24 across the forward open end of the cylindrical ampule body 12. The end portion of the crimped cap 20 is provided with a central aperture 26.

With the cylindrical ampule 12 is an elastomeric piston 28 having end flanges 30 in sliding sealing engagement with the inner wall of said ampule 12. Piston 18 is provided with a central bore 32 to receive, in sliding sealing engagement, the enlarged rear shank portion 34 of a hypodermic needle 36, said needle having a lumen 38 extending longitudinally therein from the pointed forward end thereof, terminating at and in full communication with a liquid medicament inlet port 40 in the rearward needle shank portion 34 of the enlarged diameter.

It should be noted in FIG. 3 that the enlarged rearward needle shank portion 34 is of greater axial length than that of the elastomeric piston 28 and that in the position of FIG. 3, a considerable portion of the enlarged needle shank portion 34 extends rearwardly of the piston 28 and in this position, the liquid medicament inlet port 40 lies in the axial bore 32 of said piston rearwardly of the forward face 42 of said piston, said inlet port 40 being sealed off by the wall of the piston bore 32. Then in FIG. 6, with the enlarged rearward needle shank 34 pushed forwardly so that its rear end is flush with the rear end of the piston 28, the liquid medicament inlet port 40 is exposed to liquid medicament 44 at the forward side of said piston. In other words, the forward travel of the piston shank 34 relative to piston 28 is sufficient to expose the liquid inlet port 40 to the medicament supply.

The medicament is placed in proper dosage, such as 0.5 cc in the ampule 12 under sterile conditions and, as shown in FIG. 11, the rear or right end of the ampule is closed by a frictionally held elastomeric end cap 46 which is removed prior to loading of the ampule into the injector described below.

The injector shown generally at 48 comprises a rearward spring-loaded plunger chamber 50 and a forward cylindrical ampule receiver 52. The diameter of the ampule receiver 52 is greater than that of the plunger chamber 50 so that there is provided a forwardly facing shoulder 54 constituting a seat for the rear end of the cylinder ampule 12. The forward end 52A of the receiver 52 is provided with a pair of preferably diametrically opposed lugs 56 which lie in spiral grooves 58 in an end cap 60 having a central aperture 62. When the end cap 60 is partially rotated in a counterclockwise direction, the lugs 56 and groove 58 will shift the end cap 60 forwardly. This increases the effective internal length of the cylindrical receiver 52 to permit insertion of the ampule 12 through a longitudinally elongated side opening in said receiver 52. When the ampule is in position, such as in FIG. 3, the end cap 60 is rotated oppositely, or in a clockwise direction, causing said end cap to move rearwardly a short distance and clamp the ampule 12 between the shoulder 54 and the end cap 60. When inserted in the receiver 52, the ampule 12 readily can be observed to ascertain that it is properly positioned in the receiver through the ampule loading opening 64 and also through an opposite viewing opening 66 in the side wall of the receiver 52.

Within the plunger chamber 50 is a slidable plunger 68 having a rearwardly extending rod 70 extending through a suitably aperture rear end wall 72 of the plunger chamber. Between said rear end wall 72 and the rear end of the plunger 68 is a compression spring 74 which biases the plunger 68 toward the forward end of its chamber 50. The plunger can be retracted against the force of the spring 74 by pulling a knob 76 on the rear end of the plunger rod 70.

The spring-loaded plunger 68 is held in its cocked position by a trigger element 78 on a trigger lever 80 which is pivotally mounted between its ends on a pin 82 supported by a ring bracket 84 mounted about the plunger chamber 50. Positioned about the trigger lever pivot pin 82 is a grasshopper spring 86 whose ends bear respectively against the underside of the trigger lever 80 and the outer wall of the plunger chamber 50, said spring yieldably biasing the trigger lever 80 to position of FIGS. 2 and 3.

The rear or right end of the trigger lever 80 is viewed in FIGS. 2 and 3. It is provided with a safety element 88 which is longitudinally slidable on the trigger lever between limits provided by a slot 90 in said trigger lever and a pin 92 mounted in the forward end of the trigger lever 80 and extending through said slot. The bore 94 in said safety element 88 extends rearwardly of the rear end of the trigger lever 80, providing a chamber in which is located a compression spring 96 which biases the safety element 88 rearwardly to the position shown in FIG. 2.

When the injector is cocked by drawing the plunger 68 rearwardly or to the right as viewed in FIGS. 2 and 3, the trigger element 78 will snap in front of the plunger 68 as in FIG. 3 by reason of the action of the grasshopper spring 86 on the trigger lever 80. In this cocked position, and with the safety element 88 biased rearwardly, the pin 92 therein, which extends inwardly toward the plunger chamber 50, is out of alignment with a hole or recess 98 in the wall of the piston chamber. In the position of FIG. 2 when the trigger lever is pressed in a clockwise direction, the pin 92 will engage the wall of the plunger chamber 50 before the trigger 78 can release the plunger. In order to swing the trigger lever 80 sufficiently to permit the trigger to release the plunger, it is necessary to push the safety element 88 forwardly on the trigger lever against the action of the spring 96 until the pin 92 is at the forward end of slot 90, in which position, said pin 92 is registered with the opening 98 in the wall of the plunger chamber 50 and the trigger lever 80 can be swung about its pivot 82 in a clockwise direction sufficiently to remove the trigger 78 from in front of the spring-loaded plunger, permitting the plunger to move forwardly. This dual movement of the safety element 88 in a forward direction and then at an angle in a direction transverse to the forward movement, must be accomplished in order to release the plunger 68, but it can be done conveniently with the thumb of the hand which grasps the injector. This dual movement of the safety element 88 permits the injector with an ampule loaded therein to be carried in the pocket or purse of the user, and contact with or blows against the trigger lever will not release the trigger.

The dual action required to release the plunger 68 is additionally important to prevent the user of the injector from accidentally striking the trigger lever and releasing the plunger against the needle shank and the piston 28 in the ampule 12. This safety feature is quite important, for example, in the case of diabetics who may have considerably impaired eyesight and dexterity.

The system is shown in its position in readiness for the injection of a dosage of medicament into the tissue of a patient by the patient himself or by a trained technician. The ampule 12 contains liquid medicament 44, filling the ampule forwardly of the front face 42 of the piston 28. The needle 36 has its enlarged rearward shank portion 34 supported in the piston 28, the liquid medicament inlet port 40 in the shank being sealed in the bore of said piston, and the rear portion of the shank 34 extending rearwardly of the piston in the path of movement of the spring-loaded plunger 68.

When the plunger 88 is released by a forward and then downward movement of the trigger safety element 88, when viewed as in FIG. 3, the plunger will strike the rear end of the enlarged needle shank 34. This will drive the needle forwardly or to the left relative to the piston 28. Movement of the piston shank 34 in the piston 28 is due to the frictional engagement of said piston with the inner wall of the ampule 12. This movement of the needle shank 34 independently of the piston 28 continues until the plunger 68 engages the rear or right end of said piston, whereupon both needle and piston are driven forwardly together. It has been found that if the ampules with their elastomeric, preferably rubber, pistons are unused, even for very short periods of time, the pistons will tend to seize in the cylindrical ampules. This tendency to seize or bind can be reduced by coating the outside of the piston with a silicon oil. However, the silicon oil, in a pure state, is difficult to obtain, and even when used, it is desired to provide positive means for initiating movement of the piston in the ampule.

To positively move the piston 28, the greater diameter of the rear portion 34 of the needle shank is utilized. The forward face 100 of the enlarged needle shank portion 34 is exposed to the liquid medicament 44 which is fully confined within the ampule 12. When the spring-loaded plunger 68 moves the needle shank 34 forwardly relative to the piston 28, the needle shank portion creates pressure in the liquid and that pressure, being exerted in all directions, creates sufficient rearward pressure against the forward face of the piston 28 to break the binding frictional engagement of the piston with the inner wall of the ampule 12, momentarily moving said piston 28 rearwardly as indicated by the broken lines 102 in FIG. 5. The needle shank 34 travels a short distance before the plunger 68 engages the rear or right side of the piston 28. This permits the needle to penetrate the skin at a fast rate. Medicament is not released until the needle 26 has penetrated the skin to a depth of approximately ⅛ of an inch, and the plunger 68 engages the rear face of the piston 28 approximately the same time that the inlet port 40 is exposed. Continued penetration of the tissue of the patient by the point of the needle by the pressure of plunger 68 on shank 34 to piston 28 causes the liquid medicament 44 to flow through the inlet port 40 in the needle shank 34, through the lumen 38 in the forward portion of the needle and into the tissue as needle penetration progresses.

It should be noted that when the ampule is filled with medicament there is no air space.

When the piston 28 is moved to the forward end of the ampule and the forward portion of the needle shank 34 will have entered the reduced diameter of said ampule, causing most of the liquid medicament in said reduced forward end to be pumped out of said forward end through the needle inlet port 40 and out of the needle. The result is that all but a very small quantity of liquid medicament is pumped from the ampule into the tissue of the patient, the small amount of unused or wasted medicament being compensated for in determining the amount of medicament to be loaded into the ampule at the laboratory. While the amount of liquid unused in each small dosage is not great, the provision of the described means for efficiently emptying the ampule results in an appreciable savings of sometimes quite costly medicaments. Referring to FIGS. 3 and 6, it should be noted that the rearwardly exposed portion of the needle shank 34 is such that when the shank is forced forwardly in the piston 28 to expose the liquid inlet port 40 to the medicament 44, all of the formerly exposed rearward extension of said shank lies within the bore 32 of the piston 28 so that none of the rearwardly exposed portion of said shank is brought into contact with the liquid medicament. As a result, it is unnecessary to maintain the rearwardly projecting needle shank portion in a sterile condition.

Figure 13:
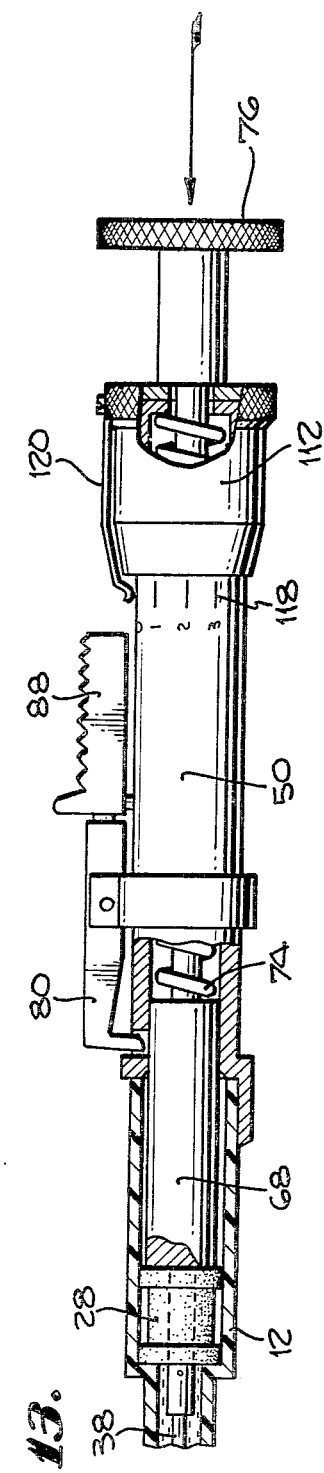
FIG. 13 is a view similar to FIG. 13 illustrating the manner in which the ampule is completely emptied.
Figure 14:
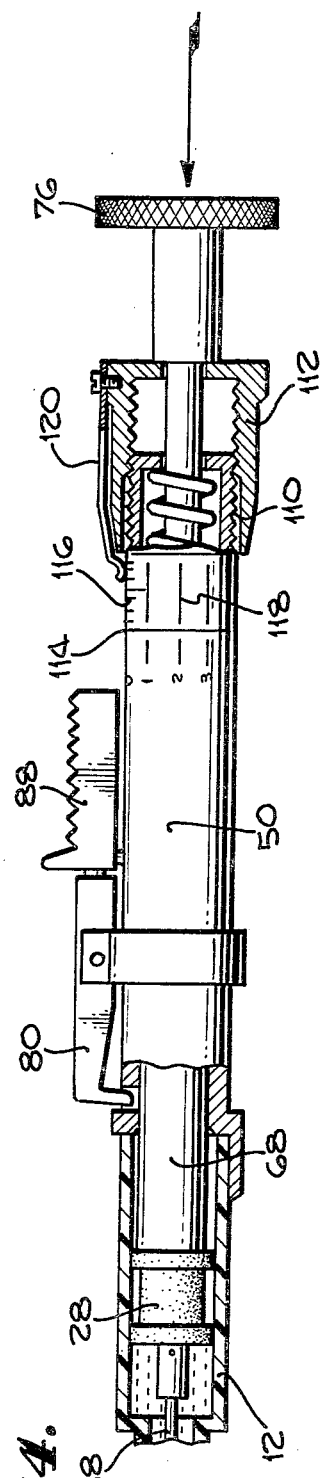
FIG. 14 is a view similar to FIGS. 12 and 13 but with the dosage control set to only partially empty an ampule.

In FIGS. 12, 13 and 14 there is illustrated an embodiment of the invention with means for conveniently and accurately adjusting the forward or working stroke of plunger 68, and as a result, the distance of travel of the piston 28, in order to vary the amount of medicament discharged from the ampule. The right or rear end of the plunger chamber 50 is provided with male threads 110 upon which an internally threaded cap 112 is mounted for longitudinal screw adjustment. When the cap 112 is turned onto the chamber 50, it moves toward the left when as viewed in FIGS. 12, 13 and 14 and when the cap is rotated counterclockwise it will move rearwardly.

The chamber 50 is provided with a relatively heavy circumferential groove 114 and to the right or rearwardly of said groove 114 are equally spaced lighter grooves 116. When the cap 112 is rotated clockwise to move it forwardly, its forward limit is indicated by coincidence of the left or forward end of the cap with the heavy groove 114. When the cap is rotated counterclockwise from the position one turn, then the left end of the cap 112 will coincide successively with the lighter grooves 116 which are equally spaced axially of the chamber 50.

The chamber 50 is also provided with a plurality of longitudinally extending grooves 118 which represent smaller dosage increments than those determined by the movement of the cap between concentric grooves. On the cap 112 is a spring finger 120 whose forward end is adapted to yieldably seat in a selected one of the longitudinal grooves 118. When the cap 112 is turned clockwise to move it forwardly or to the left as viewed in the drawings, the inside of the cup-shaped cap 112 will engage the rear or right hand of chamber 50 and further rotational adjustment of the cap is prevented. At that point the left end of the cap 112 registers with the larger circumferential groove 114 and the spring finger 120 is lodged in a longitudinal groove 118 which can be considered the zero or starting groove. In this position the plunger rod 70 is provided with its forwardmost limit of movement, which is the complete stroke of the piston 28 in its ampule.

When the cap 112 is rotated counterclockwise to move it rearwardly, the stroke of the piston rod 70 is shortened by the amount of movement of the cap axially and the ampule is capable of being emptied of only a portion of the medicament therein.

By way of illustration the ampules 12 can be produced in a size which will accommodate ½ ccs of medicament. If the medicament solution contains 40 units of medicament and it is desired to administer only 39 units, the cap 112 is rotated counterclockwise a given distance, for example, one-half turn. The horizontal grooves 118 on the sleeve 108 can be arranged to indicate smaller fractions of units of medicament. For example, for the zero position, the knob can be turned counterclockwise until the fourth longitudinal groove 118 is encountered by the spring finger 120. Naturally, if this were true the fourth groove would be located half-way about chamber 50, 180 degrees from the zero groove mentioned above. Also, if the cap 112 is rotated counterclockwise one full turn it will produce an adjustment of the cap which will shorten the effective stroke of the piston rod 70 to the extent that only 38 units of the 40 units of the filled ampule will be dispensed.

It is contemplated that ampules of uniform size be charged with medicament in units of different amounts. For example, if the ampule contained 50 units of medicament instead of the 40 referred to above, an adjustment of the cap 112 to cut down the dosage by one unit would require less movement so that the counterclockwise rotation of the cap would bring the spring finger 120 to one of the longitudinal grooves between the zero position and the half revolution position mentioned above.

Since the needle 36 in initally located with the ampule, if the movement of the piston 28 is shortened to reduce the number of units to be injected, there would be a lesser depth of penetration of the needle in the tissue. However, this can be compensated for by providing a series of, for example, six ampules with varying concentrations of medicament in increments of 10 units per ½ cc. Thus, ampules of 10, 20, 30, 40, 50 and 60 units each could be provided. If the desired dosage is 7 units the piston in a 20 unit ampule would be moved only about ⅓ of its stroke and the needle penetration would be quite short. However, if the 7 units were dispensed from a 10 unit ampule, then the stroke of the piston in the ampule would be about seven-tenths of the full stroke and the needle penetration therefore would be greater.

While the ampules and their companion injectors can be made in different sizes to accommodate different dosage quantities, ampules of 5 cc capacity provide convenient dosage units. With such a dosage, the ampule can be made, for example, of a length of about 1¼ inch and a diameter of approximately 5/16 inch. As a result, the diameter of the injector can be kept conveniently small and its length in the neighborhood of three inches, providing a compact assembly which can be manipulated conveniently and also conveniently and comfortably carried in the pocket or purse.

When used by person who has impaired eyesight or is completely blind, it can be handled by feel and easily operated by pressing the forward end against the skin and then moving the safety element on the trigger lever forwardly and thence inwardly toward the plunger chamber to release one dosage unit into the tissue without having to determine by reading or other means the measurement of a dose as in the case with a hypodermic syringe which is not pre-filled to precisely measured dosages each time it is used.

A person of impaired eyesight also can quite conveniently and safely place one of the ampules in the injector. It is a simple matter to partially rotate the end cap 60 of the injector in a counterclockwise direction to move the end cap outwardly slightly and provide accommodation for insertion of the ampule. An ampule can be inserted with the crimped cap located in the forward end of the receiver 52 merely by feeling the cap and the groove into which it is crimped, the end cap 60 of the injector can then be partially rotated clockwise to firmly seat the ampule in the injector and the plunger 68 then spring loaded to a cocked position merely by pulling rearwardly on the knob 76, the trigger 78 slipping into a plunger locking position by the action of the grasshopper spring 86 on the trigger lever 80. Actually, the loading and cocking of the injector is much simpler than the written description thereof.

It will, of course, be understood that various changes can be made in the form, details, arrangement and proportions of the various parts without departing from the spirit of the invention.

What is claimed is:

1. A self-contained hypodermic syringe dosage module for insertion into an injector comprising:
    a cylindrical barrel having open forward and rearward ends,
    the forward end of said barrel having a pierceable seal across it,
    the rearward end portion of said barrel having a piston in sliding sealing relation to the interior wall thereof,
    said barrel, between said seal and said piston, defining a medicament chamber,
    said piston having a longitudinal bore therethrough,
    a tissue piercing needle unit having a longitudinal lumen therein from the forward end and terminating short of the rear end thereof, said needle unit having a liquid inlet port in flow communication with said lumen rearwardly of its forward end,
    said needle shank portion being supported in the longitudinal bore of said piston with the inlet port of said shank portion located in and sealed by the wall of said bore,
    said needle, forwardly of said shank portion, being freely supported in said medicament chamber by said piston,
    said needle initially being movable longitudinally relative to said piston to pierce the seal at the forward end of said barrel and to expose said shank inlet port forwardly of said piston to permit flow of liquid medicament in said barrel into said port and said lumen.

2. The structure in claim 1, and said needle shank portion having an initial position in which it is extended rearwardly of said piston a distance greater than the distance between said shank liquid inlet port and the forward surface of said piston.

3. The structure in claim 1, and the frictional drag between said shank and the bore in said piston being less than that between said piston and the inner wall of said cylindrical barrel.

4. The structure in claim 2, and the frictional drag between said shank and the bore in said piston being less than that between said piston and the inner wall of said cylindrical barrel.

5. The structure in claim 1, and the diameter of said shank in the bore of said piston being greater than that of portions thereof forwardly of said piston, whereby, when the greater diameter of said shank is moved forwardly relative to said piston and into said liquid medicament chamber, the liquid is pressurized and said piston is moved to break its frictional engagement with the wall of said chamber.

6. The structure in claim 5, and said piston being movable rearwardly responsive to pressures created by said needle shank and also being movable forwardly with said shank to expel liquid medicament through the shank and the forward end of said needle.

7. The structure in claim 1, and said needle being supported only by said shank portion in the bore of said piston.

8. A hypodermic injector assembly comprising:
    a cylindrical ampule defining a chamber for medicament having a forward end with a pierceable seal and an open rear end portion with a slidable piston supporting the rear end of the hypodermic needle shank, the forward portion of the needle being disposed in the medicament chamber,
    an injector body having a cylindrical receiver for said ampule with an abutment at one end thereof,
    said cylindrical receiver having an ampule lock engageable with the ampule to releasably hold the ampule against said abutment in said receiver,
    and power means carried by said body rearwardly of said ampule receiver and positioned to engage and forwardly project said hypodermic needle shank.

9. The structure in claim 8, and said receiver having a side opening for the insertion of an ampule,
    and said ampule lock being disposed at the forward end of said receiver and axially adjustable relative to said receiver from a forward receiver lengthening position relative to said ampule insertion opening, to a rearward receiver shortening position.

10. The structure in claim 8, and said ampule lock comprising a forward end member telescopically and rotatably fitting the forward end of said receiver,
    and said receiver and ampule lock having one each of a spiral guide and a guide follower to project and retract the ampule lock upon rotation thereof.

11. The structure in claim 8, and a trigger carried by said body and movable from an "on" position to restrain, to an "off" position to release, said power means.

12. The structure in claim 9, and said trigger, in its movement from the "on" to the "off" positions having a path of travel out of and into the path of forward projection of said power means.

13. A hypodermic injector assembly comprising:
    an injector body,
    a medicament ampule having a movable medicament pressurizing element and an injection needle,
    a plunger movably carried by said body to move said pressurizing element, means biasing said pressurizing element toward exerting pressure upon medicament in said ampule, a trigger movable in a given direction to releasably restrain said plunger, and a trigger safety device normally locking said trigger against movement and being movable in a direction other than said given direction of said trigger before the trigger can be moved.

14. The structure in claim 13, and said member movably carried by said body and said biasing means comprising respectively, a plunger and a spring therefor, and said trigger having a portion lying in front of said plunger when the plunger is retracted against said spring, a release for said trigger portion movable transversely of the direction of movement of said plunger, and a safety lock for said trigger release, the trigger release having means requiring a first movement at an angle to its transverse movement before said transverse movement can be accomplished.

15. The structure in claim 13, and said trigger comprising a lever pivotally supported by said injector body and having a detent movable into and out of the path of movement of said plunger, a trigger actuator movable relative to said lever from a "lock" position to a "release" position, and said lever and detent, when the trigger actuator is in its "lock" position, is locked to prevent movement of said detent from the path of movement of said plunger.

16. The structure in claim 15, and said trigger actuator being mounted on said lever and movable relative thereto.

17. A hypodermic injector comprising:

an injector body having a medicament holder for supplies of medicament solutions of varied concentrations for a given volume and having a plunger chamber, a plunger slidable in said plunger chamber, a plunger rod connected to and movable with said plunger and extending rearwardly from said plunger chamber, a cap threadedly mounted on the rear end of said plunger chamber for longitudinal adjustment relative thereto, said plunger rod having an abutment engagable with said cap to limit the forward movement of the rod, said plunger chamber having longitudinally disposed indica thereon within the range of longitudinal adjustment of said cap to indicate cap adjustment or predetermined medicament unit relationships to plunger rod travel, at least one of said plunger chamber and cap having circumferentially disposed indicia to indicate other medicament unit relationships to plunger rod travel, at least one set of said indicia being related to one of a plural number of medicament unit concentrations for said given liquid volume.

18. A hypodermic injector comprising:

an injector body having a medicament holder for supplies of solute medicament in different proportions to a solvent vehicle, said body having a plunger chamber and a plunger slidable therein, a plunger rod connected to and movable with said plunger and extending rearwardly from said plunger chamber, a cap threadedly mounted on the rear end of said plunger chamber for longitudinal adjustment relative thereto, said plunger rod having an abutment engagable with said cap to limit the forward movement of the rod, said plunger chamber having longitudinally disposed indica thereon within the range of adjustment of said cap to correlate plunger and cap positions relative to solutions having given proportions of medicament to solvent, and at least one of said plunger chamber and cap having circumferentially disposed indicia to indicate the number of units to be dispensed from the solution of given medicament proportions when the cap and plunger have been correlated to a solution of given proportions.

19. The structure in claim 1, and said barrel having a cylindrical forward portion of an inner reduced diameter less than that of said piston, said needle shank portion being of enlarged diameter rearwardly of the forward end of the needle and having a cylindrical diameter to be accommodated, at the forwardmost position of the needle in the cylindrical barrel, in the forward inner reduced diameter portion of said barrel with the inlet port of said shank in liquid flow communication with the space between said shank and said inner reduced diameter of said barrel, the shank of said needle being supported for longitudinal movement in said piston bore between given rearward and forward limits, and said shank, between said limits being of greater diameter than the forward end portion of the needle.

20. The structure in claim 19, and said piston having a forward face defining, with said cylindrical barrel, portions of a sterile medicament chamber, said piston having a rearward face exposed in a non-sterile area adjacent the rear of said barrel, said shank, in its rearward limit of movement in said piston, extending rearwardly of said piston into said non-sterile area, and in its forward limit of movement in said piston, that portion of the shank which has been extended into said non-sterile area being sealed from the sterile medicament chamber in and by said piston.

21. In an hypodermic syringe device, a complete self-contained medicament ampule insertable in and removable from an injector and having a cylindrical barrel with an open rear end, the barrel having a forward end portion with an external flange having a rearwardly facing side wall, a pierceable seal across the forward end of said barrel, a centrally apertured cap over the forward end of the barrel and said seal and having a side wall about the forward end of the barrel and crimped behind the rearwardly facing side wall of said flange, a piston movable in said barrel in sealed relation to the inner wall thereof, and a hollow needle unit in said barrel behind said seal and having a rearwardly disposed liquid entry and being supported merely by and movable with said piston.

* * * * *